(12) United States Patent
Chen et al.

(10) Patent No.: US 7,462,723 B2
(45) Date of Patent: Dec. 9, 2008

(54) IMIDAZOLAMINO COMPOUNDS

(75) Inventors: Chiung-Tong Chen, Taipei (TW);
Wen-Tai Li, Hsinchu (TW); Der-Ren Hwang, Keelung (TW); Chu-Chung Lin, Taichung (TW)

(73) Assignee: National Health Research Institutes, Zhunan Town, Miaoli County (TW)

( * ) Notice: Subject to any disclaimer, the term of this patent is extended or adjusted under 35 U.S.C. 154(b) by 0 days.

(21) Appl. No.: 11/472,064

(22) Filed: Jun. 21, 2006

(65) Prior Publication Data
US 2006/0241140 A1 Oct. 26, 2006

Related U.S. Application Data

(62) Division of application No. 10/649,233, filed on Aug. 26, 2003, now Pat. No. 7,109,227.

(60) Provisional application No. 60/406,363, filed on Aug. 26, 2002.

(51) Int. Cl.
*A61K 31/427* (2006.01)
*C07D 417/04* (2006.01)

(52) U.S. Cl. ...................... 548/202; 514/365

(58) Field of Classification Search ............ 548/202
See application file for complete search history.

(56) References Cited

FOREIGN PATENT DOCUMENTS

WO   WO 99/51224   10/1999

OTHER PUBLICATIONS

Golub et al., Science, vol. 286, Oct. 15, 1999, pp. 531-537.*
Beyer et al., Liebigs Ann. Chem. 748:109-122, 1971.
Beyer et al., Chemische Berichte 101:3151-3162, 1968.
Bruckner et al., Liebigs Ann. Chem. 639-649, 1979.
Hetzheim et al., Chem. Ber. 103:3533-3542, 1970.
Hezheim et al., Chem. Ber. 103:2845-2852, 1970.
Hetzheim et al., Chem. Ber. 100:3418-3426, 1967.
Honeck et al, Chem. Ber. 104:407-411, 1971.
Krimer et al., Chemistry of Heterocyclic Compounds 32:1035-1039, 1996.
Molina et al., Heterocycles 37:997-1018, 1994.
Yun et al., "Streamlined Synthesis of Substituted 2-Aminothiazoles Using Tandem Precipitative and Polymer-Assisted Reactions", Biotechnology and Bioengineering 71:9-18, 2000.
CA Registry No. 388609-03-8, entry date into Registry file on STN is Jan. 31, 2002.
CA Registry No. 388093-36-5, entry date into Registry file on STN is Jan. 30, 2002.
CA Registry No. 352656-72-5, entry date into Registry file on STN is Aug. 27, 2001.
Miyamoto, Journal of Heterocyclic Chemistry (Jan.-Feb. 2002), 39(1), pp. 157-162.
CA Registry No. 319429-16-8, entry date into Registry file on STN is Feb. 2, 2001.
Lalezari et al., CA 81:105459, 1974.
Harmon et al., Journal of Pharmaceutical Sciences (1970), 59(5), p. 724.
Krimer et al., CA 126:89305, 1996.

* cited by examiner

*Primary Examiner*—Laura L. Stockton
(74) *Attorney, Agent, or Firm*—Occhiuti Rohlicek & Tsao LLP

(57) ABSTRACT

The invention relates to novel imidazolamino compounds. Also disclosed are methods of treating cancer by using one of these compounds and pharmaceutical compositions containing one of these compounds.

11 Claims, No Drawings

IMIDAZOLAMINO COMPOUNDS

CROSS REFERENCE TO RELATED APPLICATIONS

This application is a divisional application of U.S. Utility Application Ser. No.: 10/649,233, filed Aug. 26, 2003, now U.S. Pat. No. 7,109,227, which in turn claims priority to U.S. Provisional Application Ser. No. 60/406,363, filed Aug. 26, 2002, the contents of which are incorporated herein by reference.

BACKGROUND

Cancer is one of the most common causes of death in developed countries. Despite continuing advances, most existing cancer treatments have undesirable side effects and limited efficacy. Identifying new effective anti-cancer drugs has always been the focus of cancer research.

Imidazolamino compounds have been demonstrated in animal models of non-insulin-dependent diabetes mellitus to both improve insulin sensitivity and promote weight loss selectively from adipose tissue. Indeed, some of them are anti-diabetic drugs. See, e.g., J. Med. Chem., 2001, 44, 1231-1248. However, no imidazolamino compounds have been reported to possess anti-cancer activities.

SUMMARY

One aspect of this invention relates to imidazolamino compounds of formula (I)

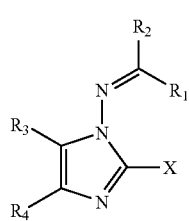

(I)

In formula (I), X is —$NR_aR_b$ or —$N=CR_cR_d$, in which each of $R_a$ and $R_b$, independently, is hydrogen, halo, alkyl, haloalkyl, arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl; and each of $R_c$ and $R_d$, independently, is hydrogen; halo; alkyl; heteroaryl; phenyl optionally substituted with hydroxy, halo, alkyl, haloalkyl, alkoxy, or amino; phenylsulfonyl substituted with cyano, halo, oxo, or amino; phenylcarbonyl substituted with cyano, halo, oxo, or amino; naphthylsulfonyl substituted with cyano, halo, oxo, or amino; naphthylcarbonyl substituted with cyano, halo, oxo, or amino; or alkyl optionally substituted with halo, phenyl or imidazolyl, or phenyl or imidazolyl optionally substituted with alkyl, halo, or hydroxy. $R_1$ is cycloalkyl, cycloalkenyl, aryl, heteroaryl, or heterocyclyl, optionally fused to aryl, heteroaryl, cycloalkyl, or heterocyclyl; hydrogen; halo; alkyl; haloalkyl; alkenyl; or alkynyl. $R_2$ is hydrogen, alkyl, cycloalkyl, cycloalkenyl, phenyl, thienyl, thiazolyl, anthryl, or quinolyl, optionally substituted with hydroxy, halo, cyano, alkyl, haloalkyl, nitro, or alkoxy. $R_3$ is hydrogen, alkyl, or phenyl optionally substituted with hydroxy, halo, alkyl, haloalkyl, cyano, nitro, or alkoxy. $R_4$ is biphenyl, thienyl, pyridinyl, thiazolyl, anthryl, naphthyl, or quinolyl, optionally substituted with hydroxy, halo, alkyl, haloalkyl, nitro, or alkoxy, when $R_2$ is thienyl, thiazolyl, anthryl, or quinolyl, optionally substituted with hydroxy, halo, alkyl, haloalkyl, cyano, nitro, or alkoxy; is diphenyl, thienyl, pyridinyl, thiazolyl, anthryl, naphthyl, or quinolyl, optionally substituted with hydroxy, halo, alkyl, haloalkyl, cyano, nitro, or alkoxy, when $R_2$ is phenyl optionally substituted with hydroxy, alkyl, haloalkyl, or alkoxy; is pyridinyl, thiazolyl, anthryl, naphthyl, or quinolyl, optionally substituted with hydroxy, halo, alkyl, haloalkyl, nitro, or alkoxy, when $R_2$ is phenyl optionally substituted with chloro, bromo, iodo, or nitro; is phenyl optionally substituted with hydroxy, halo, alkyl, haloalkyl, nitro, or alkoxy when $R_2$ is phenyl substituted with fluoro, alkyl, or haloalkyl; or is alkyl, cycloalkyl, cycloalkenyl, or heterocyclyl optionally substituted with hydroxy, halo, alkyl, cyano, nitro, haloalkyl or alkoxy, when $R_2$ is hydrogen, alkyl, cycloalkyl, cycloalkenyl, thienyl, thiazolyl, anthryl, or quinolyl, optionally substituted with hydroxy, halo, alkyl, haloalkyl, cyano, or alkoxy.

The term "halo" refers to any radical of fluorine, chlorine, bromine or iodine. The term "alkyl," independently or as a prefix (e.g., alkoxy) or surfix (e.g., haloalkyl), refers to a hydrocarbon chain that may be a straight chain or branched chain of $C_{1-12}$. The term "alkylene" refers to a divalent alkyl (i.e., —R—) of $C_{1-12}$. The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

Subsets of the compounds include those in which $R_2$ is thienyl, thiazolyl, anthryl, or quinonlyl, optionally substituted with hydroxy, halo, alkyl, haloalkyl, nitro, or alkoxy; or phenyl substituted with hydroxy, fluoro, chloro, bromo, alkyl, or alkoxy; those in which $R_4$ is phenyl, pyridinyl, thiazolyl, anthryl, or quinonlyl, optionally substituted with hydroxy (e.g., hydroxyanthryl), halo (e.g., chloropyridinyl), alkyl (e.g., alkylphenyl), haloalkyl, nitro (e.g., nitrothiazolyl), or alkoxy; and those in which X is $NH_2$; those in which $R_1$ is hydrogen or heteroaryl; and $R_3$ is hydrogen or phenyl.

Specific examples of these compounds include

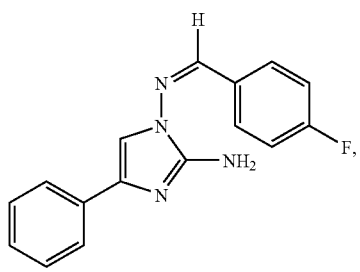

-continued
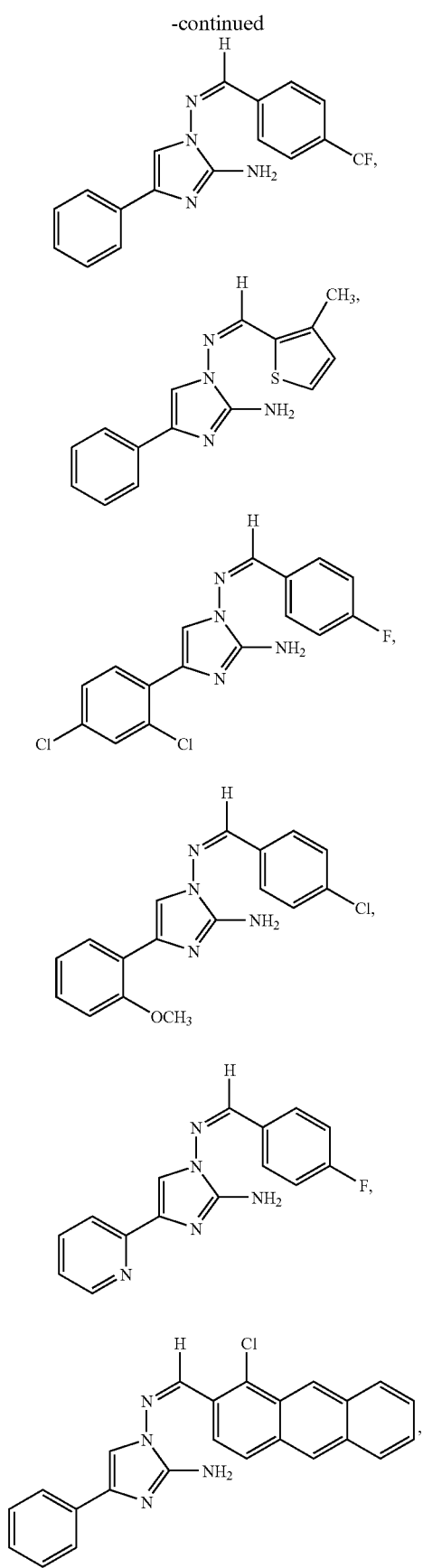
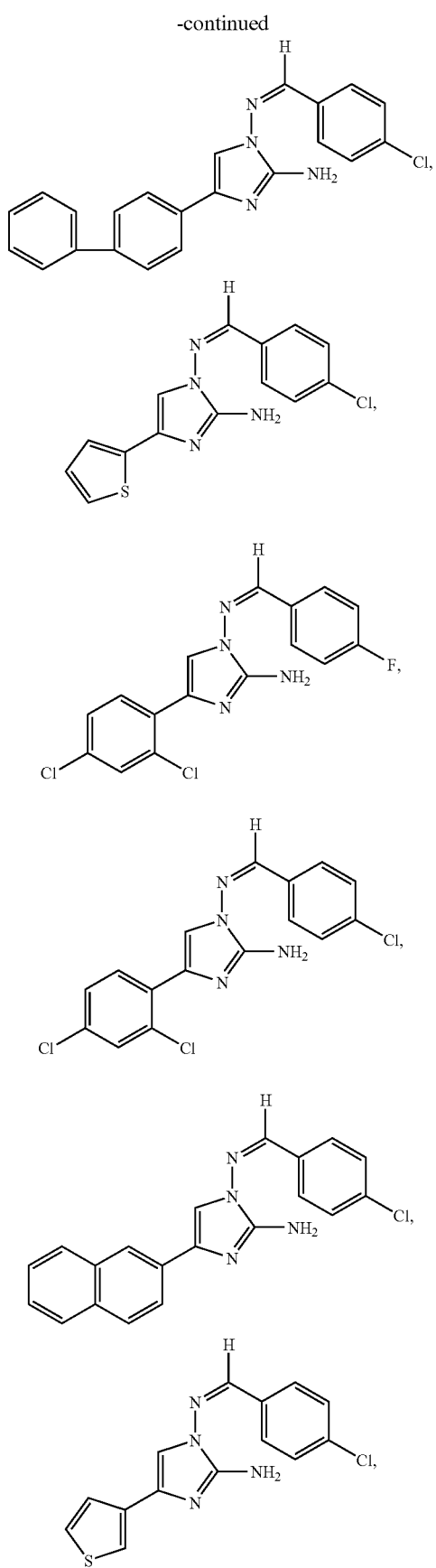

-continued
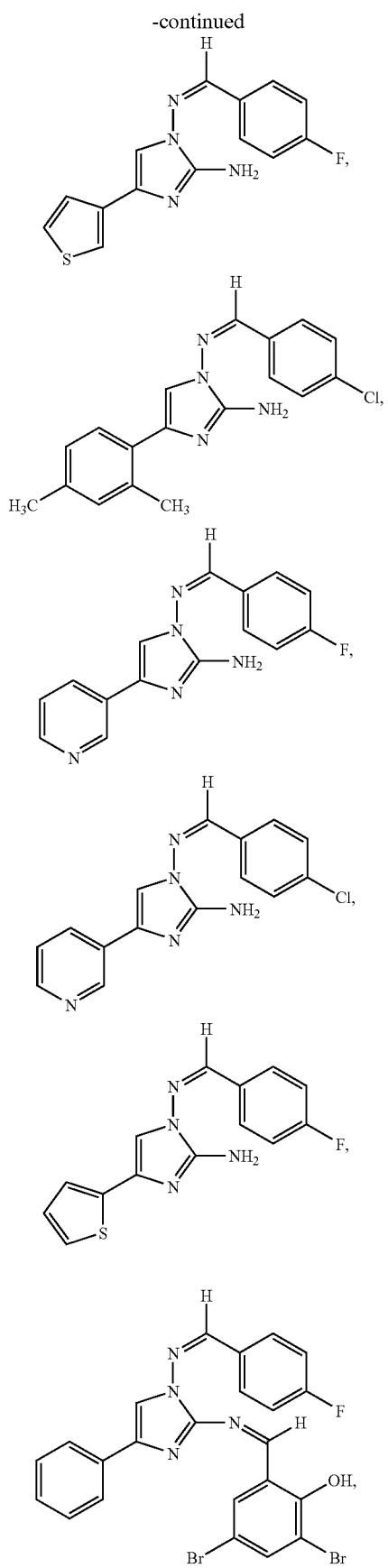
-continued
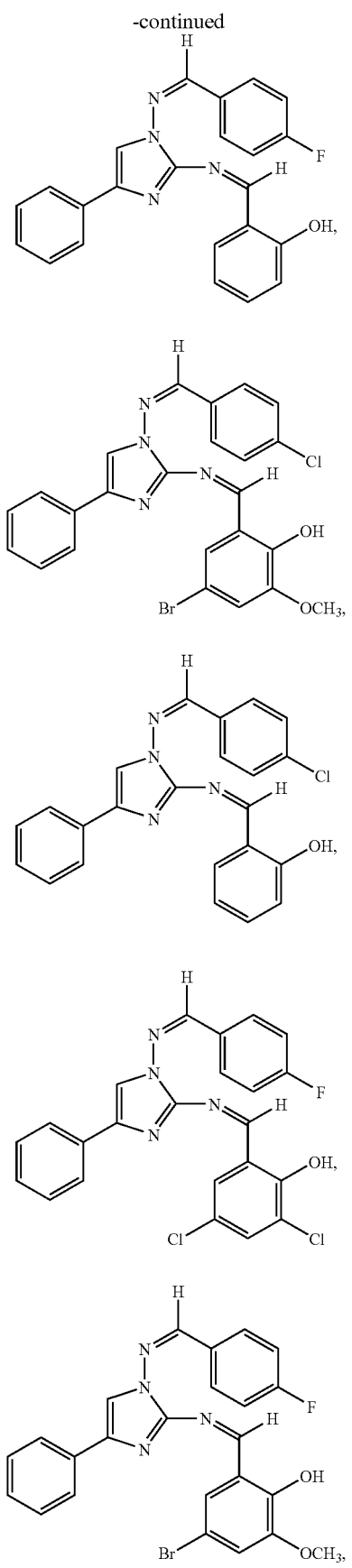

-continued

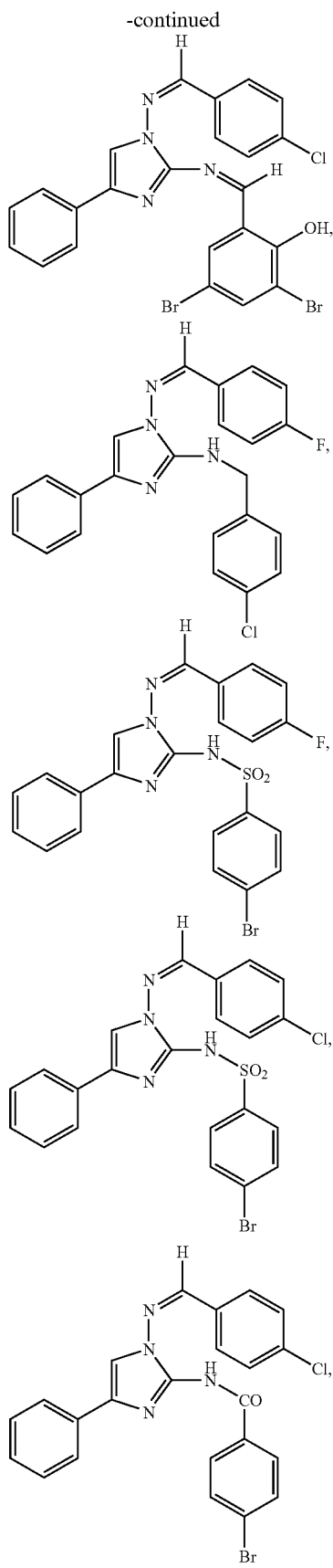

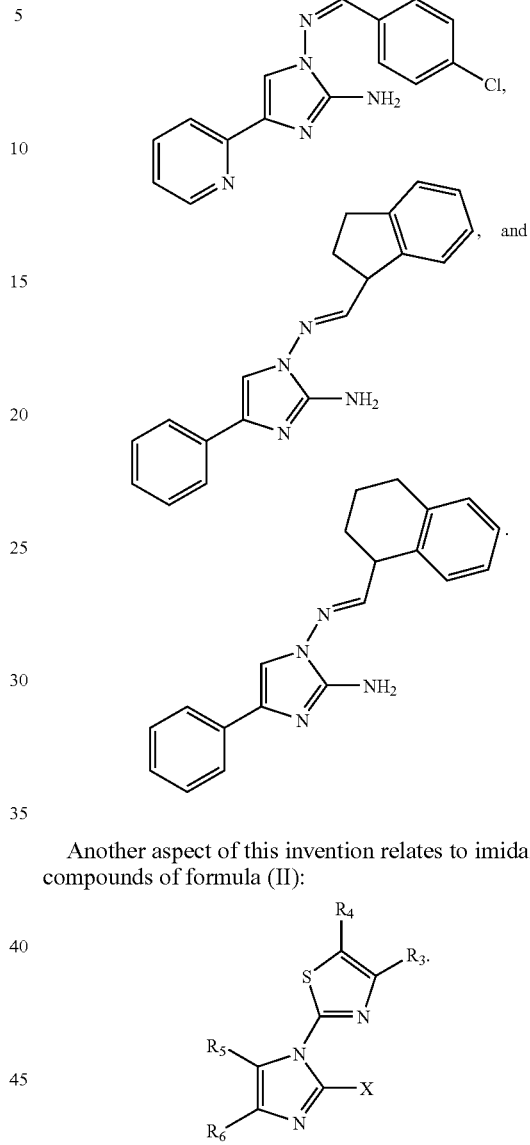

Another aspect of this invention relates to imidazolamino compounds of formula (II):

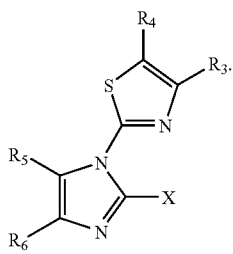

(II)

In formula (II), X is —NR$_a$R$_b$ or —N=CR$_c$R$_d$, in which each of R$_a$ and R$_b$, independently, is hydrogen, halo, alkyl, or haloalkyl; arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl, and each of R$_c$ and R$_d$, independently, is hydrogen; halo; alkyl; heteroaryl; phenyl optionally substituted with hydroxy, halo, alkyl, haloalkyl, alkoxy, or amino; phenylsulfonyl substituted with cyano, halo, oxo, or amino; phenylcarbonyl substituted with cyano, halo, oxo, or amino; naphthylsulfonyl substituted with cyano, halo, oxo, or amino; naphthylcarbonyl substituted with cyano, halo, oxo, or amino; or alkyl optionally substituted with halo, phenyl or imidazolyl, or phenyl or imidazolyl optionally substituted with alkyl, halo, or hydroxy. Each of R$_1$ and R$_2$, independently, is hydrogen, alkyl, or haloalkyl. R$_3$ is alkyl, phenyl, thienyl, pyridinyl, thiazolyl, cycloalkyl, cycloalkenyl, benzofuranyl, indolyl, pyrazinyl, pyrimidinyl, pyrrolyl, N-methylpyrrolyl, isothiazolyl, oxadiazolyl, furyl, isoazolyl, oxazolyl, or heterocyclyl optionally substituted with halo, alkyl, haloalkyl, hydroxy, or amino. $R_4$ is hydrogen, alkyl, hydroxy, or amino. $R_5$ is hydrogen, alkyl, or aryl optionally substituted with hydroxy, halo, alkyl, haloalkyl, or amino. $R_6$ is hydrogen, fluorophenyl, naphthyl, thienyl, pyridinyl, furyl, thiazolyl cycloalkyl, cycloalkenyl, benzofuranyl, indolyl, pyrazinyl, pyrimidinyl, pyrrolyl, N-methylpyrrolyl, isothiazolyl, oxadiazolyl, isoazolyl, oxazolyl, or heterocyclyl when $R_3$ is alkyl optionally substituted with halo, hydroxy, or amino, or is phenyl optionally substituted with halo, hydroxy, amino, or alkyl; and $R_5$ is hydrogen, alkyl, or aryl optionally substituted with hydroxy, alkyl, or amino, or is phenyl optionally substituted with hydroxy, halo, alkyl, haloalkyl, or amino when $R_3$ is thienyl, pyridinyl, or thiazolyl, optionally substituted with halo, alkyl, haloalkyl, or hydroxy, and $R_5$ is hydrogen, alkyl, or phenyl optionally substituted with hydroxy, halo, alkyl, haloalkyl, or amino Subset of the compounds of formula (II) include those in which $R_6$ is hydrogen, fluorophenyl, naphthyl, thienyl, pyridinyl, furyl, or thizaolyl, when $R_3$ is alkyl optionally substituted with halo, hydroxy, or amino, or is phenyl optionally substituted with halo, hydroxy, amino, or alkyl; and when $R_5$ is hydrogen, alkyl, or aryl optionally substituted with hydroxy, alkyl, or amino; those in which X is $NH_2$; those in which $R_4$ is H; those in which $R_3$ is phenyl or alkyl, optionally substituted with halo; and $R_5$ is hydrogen or phenyl.

Specific examples of the compound of formula (II) include

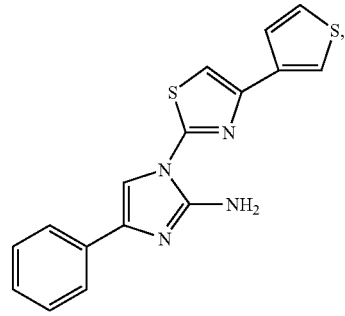

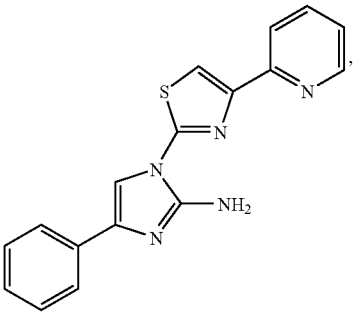

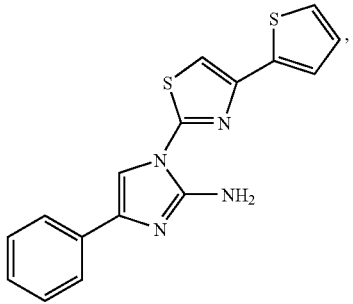

-continued

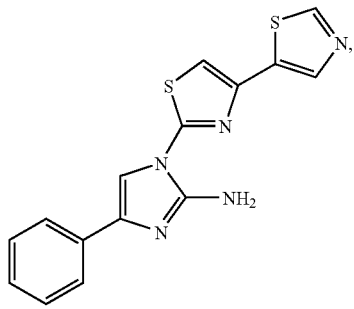

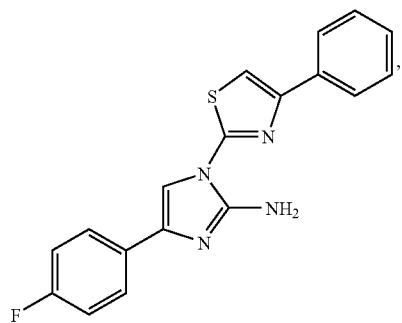

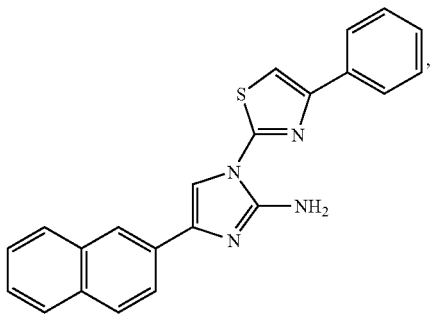

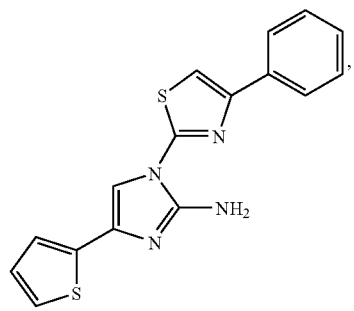

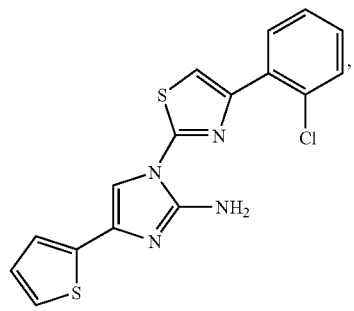

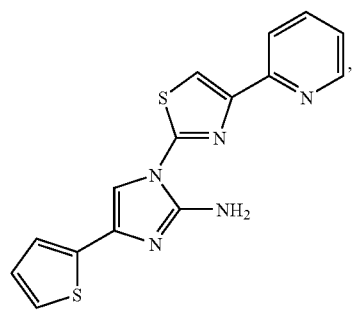
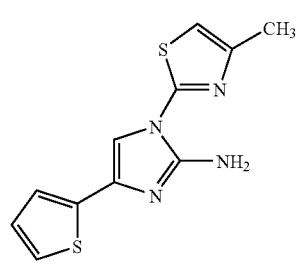
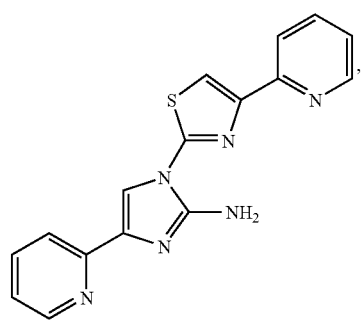
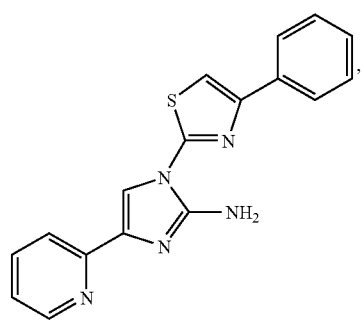
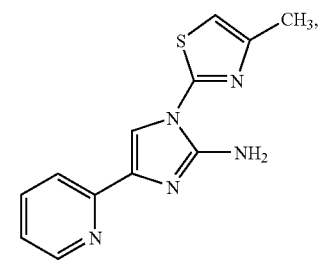
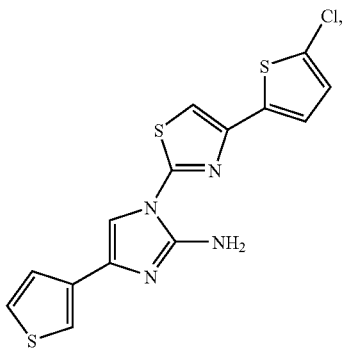
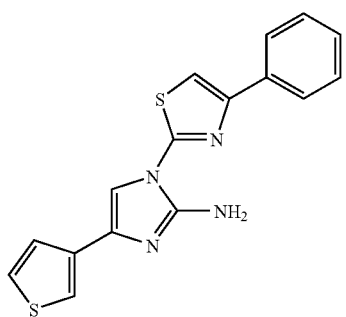
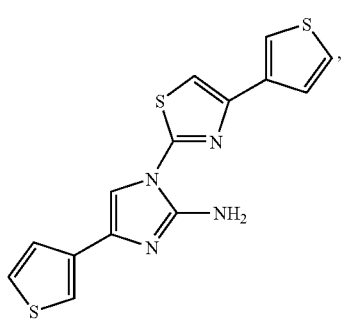
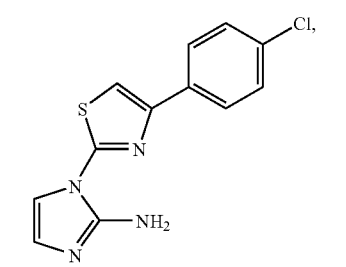
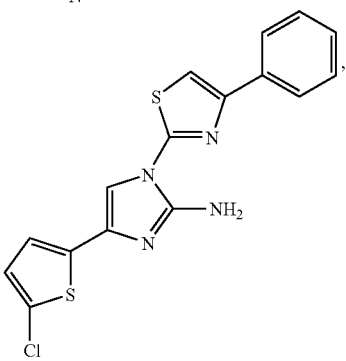

-continued

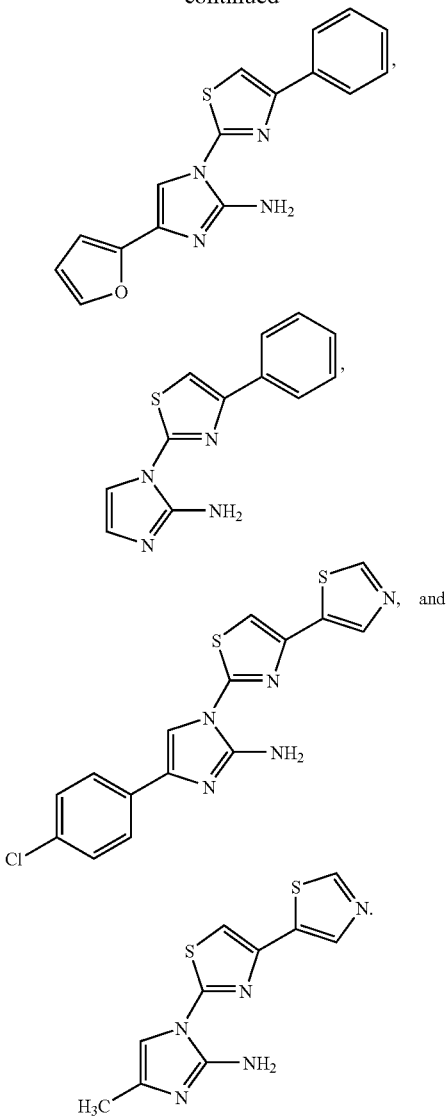

Still another aspect of this invention relates to imidazolamino compounds of formula (III):

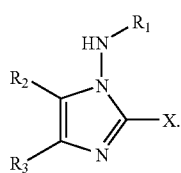

(III)

In formula (III), X is —NR$_a$R$_b$ or —N=CR$_c$R$_d$, in which each of R$_a$ and R$_b$, independently, is halo or haloalkyl, arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl, or phenyl optionally substituted with halo; and each of R$_c$ and R$_d$, independently, is hydrogen, halo, or phenyl optionally substituted with hydroxy, halo, alkyl, haloalkyl, alkoxy, or amino; phenylsulfonyl substituted with cyano, halo, oxo, or amino; phenylcarbonyl substituted with cyano, halo, oxo, or amino; naphthalenylsulfonyl substituted with cyano, halo, oxo, or amino; naphthylcarbonyl substituted with cyano, halo, oxo, or amino; or alkyl optionally substituted with halo, phenyl optionally substituted with alkyl, halo, or hydroxy, or imidazolyl optionally substituted with alkyl, halo, or hydroxy; R$_1$ is alkyl, phenyl, haloalkylphenyl, phenylalkyl, diphenylalkyl, pyridinylalkyl, phenyloxadiazolylalkyl, phenylcarbonyl, furylcarbonyl, thienylcarbonyl, isoxazolylcarbonyl, phenylaminocarbonyl, or phenylsulfonyl, optionally substituted with alkoxy, halo, cyano, nitro, or haloalkyl; or hydrogen; R$_2$ is hydrogen, alkyl, phenyl, furyl, thienyl, pyridinyl, oxadiazolyl, or isoxazolyl, optionally substituted with halo; and R$_3$ is hydrogen, furyl, thienyl, pyridinyl, oxadiazolyl, or isoxazolyl, optionally substituted with halo or alkyl. Alternatively, X is —NR$_a$R$_b$ or —N=CR$_c$R$_d$, in which each of R$_a$ and R$_b$, independently, is halo or haloalkyl, arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl, or phenyl optionally substituted with halo; and each of R$_c$ and R$_d$, independently, is hydrogen, halo, or phenyl optionally substituted with hydroxy, halo, alkyl, haloalkyl, alkoxy, or amino; phenylsulfonyl substituted with cyano, halo, oxo, or amino; phenylcarbonyl substituted with cyano, halo, oxo, or amino; naphthalenylsulfonyl substituted with cyano, halo, oxo, or amino; naphthylcarbonyl substituted with cyano, halo, oxo, or amino; or alkyl optionally substituted with halo, phenyl optionally substituted with alkyl, halo, or hydroxy, or imidazolyl optionally substituted with alkyl, halo, or hydroxy; R$_1$ is alkyl, haloalkylphenyl, phenylalkyl, diphenylalkyl, pyridinylalkyl, phenyloxadiazolylalkyl, phenylcarbonyl, furylcarbonyl, thienylcarbonyl, isoxazolylcarbonyl, phenylaminocarbonyl, or phenylsulfonyl, optionally substituted with alkoxy, halo, nitro, or haloalkyl; or hydrogen; R$_2$ is hydrogen, alkyl, phenyl, furyl, thienyl, pyridinyl, oxadiazolyl, or isoxazolyl, optionally substituted with halo; and R$_3$ is phenyl optionally substituted with halo, alkoxy or alkyl. As yet another alternative, X is —NR$_a$R$_b$ or —N=CR$_c$R$_d$, in which each of R$_a$ and R$_b$, independently, is hydrogen or alkyl, arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl, or phenyl optionally substituted with halo; and each of R$_c$ and R$_d$, independently, is hydrogen, halo, or phenyl optionally substituted with hydroxy, halo, alkyl, haloalkyl, alkoxy, or amino; phenylsulfonyl substituted with cyano, halo, oxo, or amino; phenylcarbonyl substituted with cyano, halo, oxo, or amino; naphthalenylsulfonyl substituted with cyano, halo, oxo, or amino; naphthylcarbonyl substituted with cyano, halo, oxo, or amino; or alkyl optionally substituted with halo, phenyl optionally substituted with alkyl, halo, or hydroxy, or imidazolyl optionally substituted with alkyl, halo, or hydroxy; R$_1$ is hydrogen, alkyl, phenyl, haloalkylphenyl, phenylalkyl, diphenylalkyl, pyridinylalkyl, phenyloxadiazolylalkyl, phenylcarbonyl, furylcarbonyl, thienylcarbonyl, isoxazolylcarbonyl, phenylaminocarbonyl, or phenylsulfonyl, in which phenyl, furyl, thienyl, pyridinyl, oxadiazolyl, or isoxazolyl is optionally substituted with alkoxy, halo, nitro, or haloalkyl; R$_2$ is hydrogen, alkyl, phenyl, furyl, thienyl, pyridinyl, oxadiazolyl, or isoxazolyl, optionally substituted with halo; and R$_3$ is hydrogen, furyl, thienyl, pyridinyl, oxadiazolyl, or isoxazolyl, optionally substituted with halo or alkyl.

Subsets of the compounds of formula (III) includes those in which X is NH$_2$; those in which R$_2$ is hydrogen; and those in which R$_3$ is phenyl, furyl, or thienyl. Specific examples of these compounds include
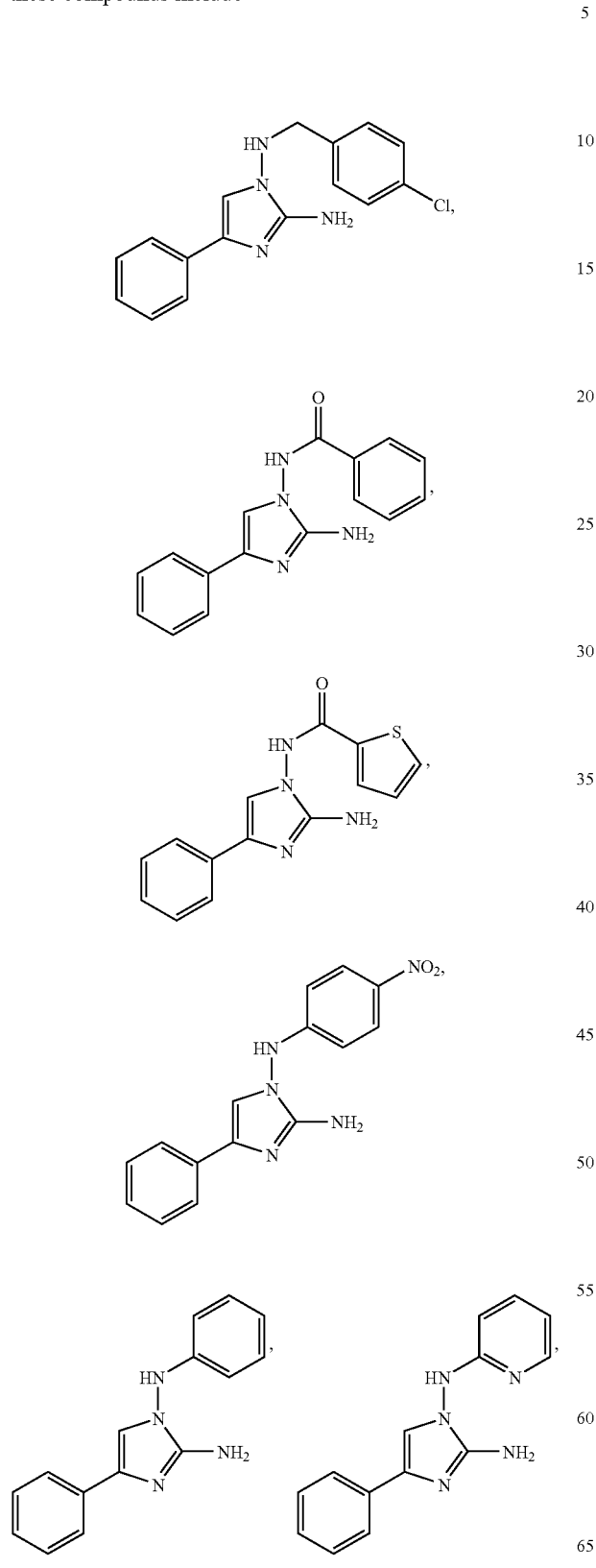
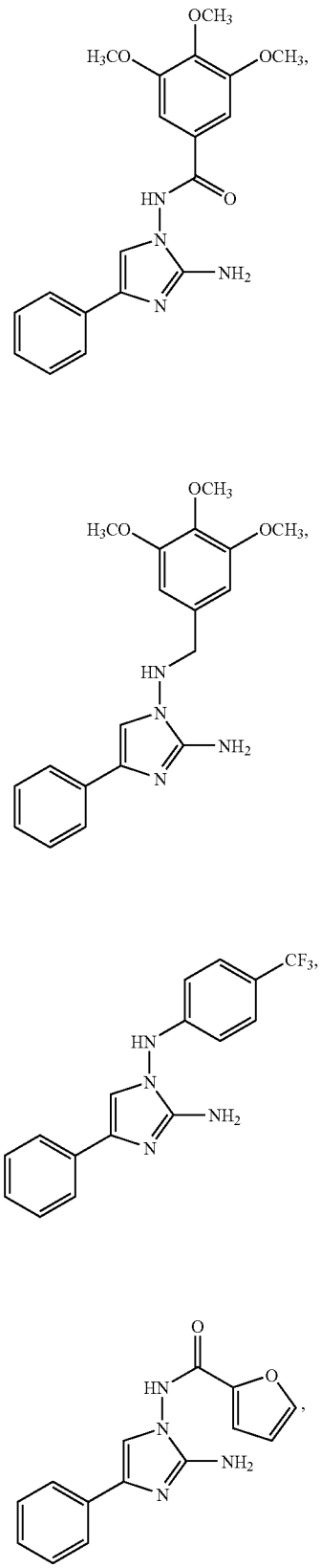

-continued
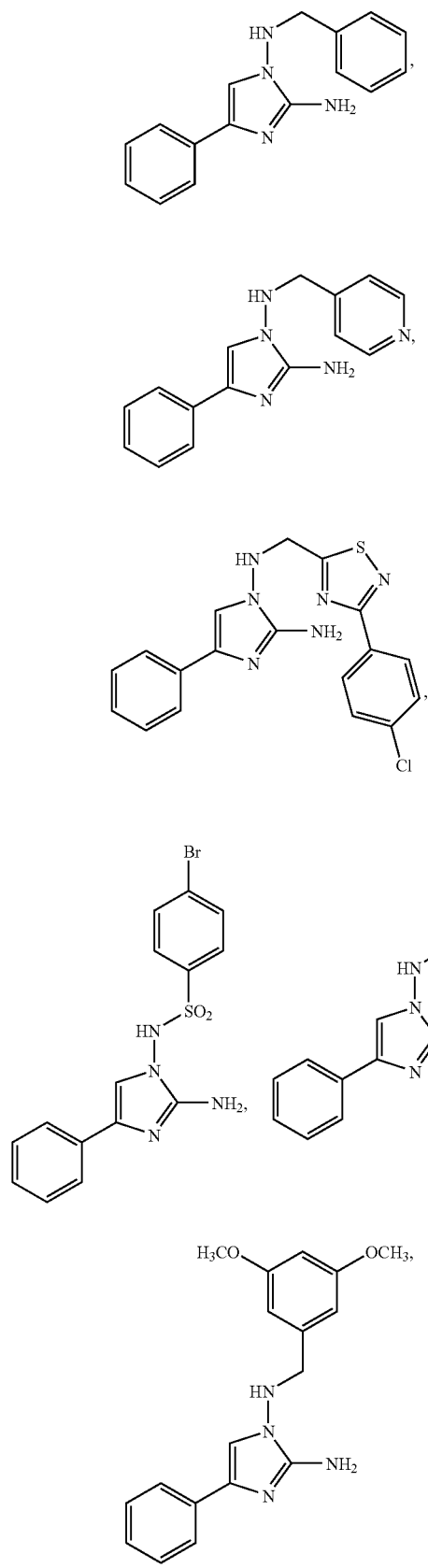
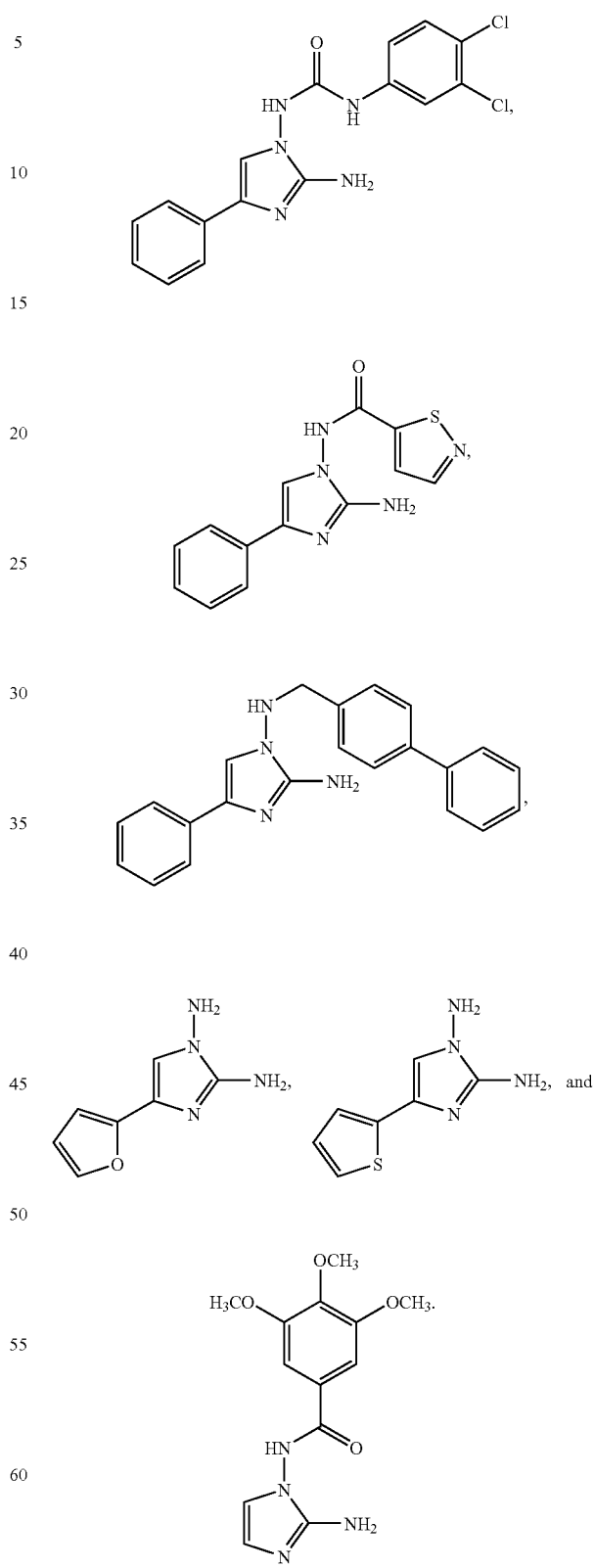
The imidazolamino compounds described above include their salts, if applicable. Such a salt, for example, can be formed between a positively charged substituent, e.g., amino, and an anion. Suitable anions include, but are not limited to, chloride, bromide, iodide, sulfate, nitrate, phosphate, or acetate. Likewise, a negatively charged substituent (e.g., carboxylate) can form a salt with a cation. Suitable cations include, but are not limited to, sodium ion, potassium ion, magnesium ion, calcium ion, and an ammonium cation such as tetramethylammonium ion.

The compounds of this invention can be used as anti-cancer drugs. Thus, also within the scope of this invention are pharmaceutical compositions each containing a pharmaceutically acceptable carrier and one of the above-described compounds; and methods for treating cancer, which include administering to a subject in need thereof an effective amount of an above-described compound.

The details of several embodiments of the invention are set forth in the accompanying description below. Other features, objects, and advantages of the invention will be apparent from the description and from the claims.

DETAILED DESCRIPTION

Imidazolamino compounds of this invention generally can be synthesized from an aminoguanidine compound by first coupling it with a carbonyl containing compound (e.g., an aldehyde) to form an iminoguinidine adduct. The iminoguinidine adduct can then react with a haloaceto compound (e.g., bromoacetofuryl) via a ring-form mechanism to form an imidazolyl ring. Shown below is Scheme 1, which depicts a method for preparing some imidazolamino compounds of this invention.

Starting materials containing different substituents on $Ar_1$ and $Ar_2$ can be used to prepare imidazolamino compounds containing various substituents on $Ar_1$ or $Ar_2$ by following the same reaction scheme.

The 2-amino group in the imidazolamino compounds can be modified as shown below in Schemes 2, 3, and 4:

Scheme 2

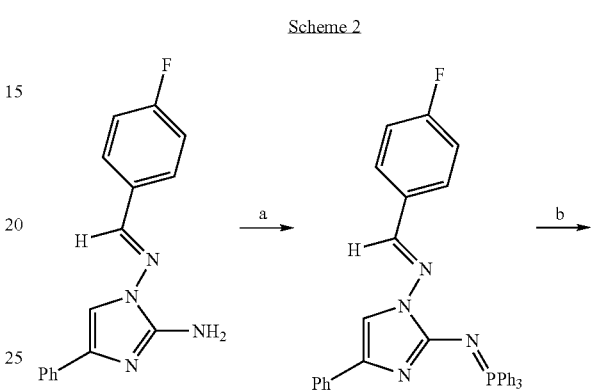

a $Ph_3PBr_2$, $Et_3N$, benzene;
b benzaldehyde, toluene, 3 h.

Scheme 1

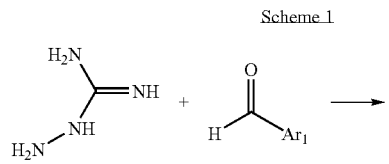

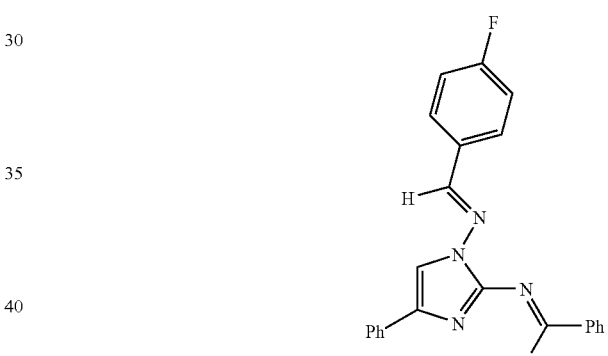

Scheme 3

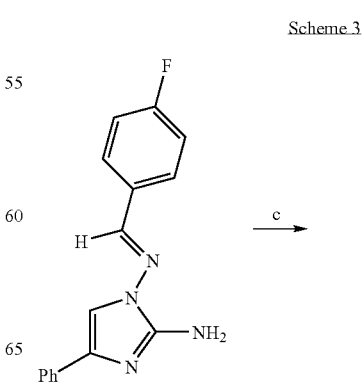

-continued

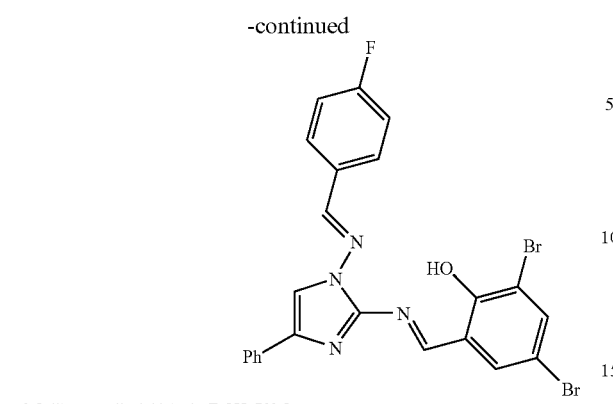

c 3,5-dibromosalicylaldehyde, EtOH, 70° C.

Scheme 4

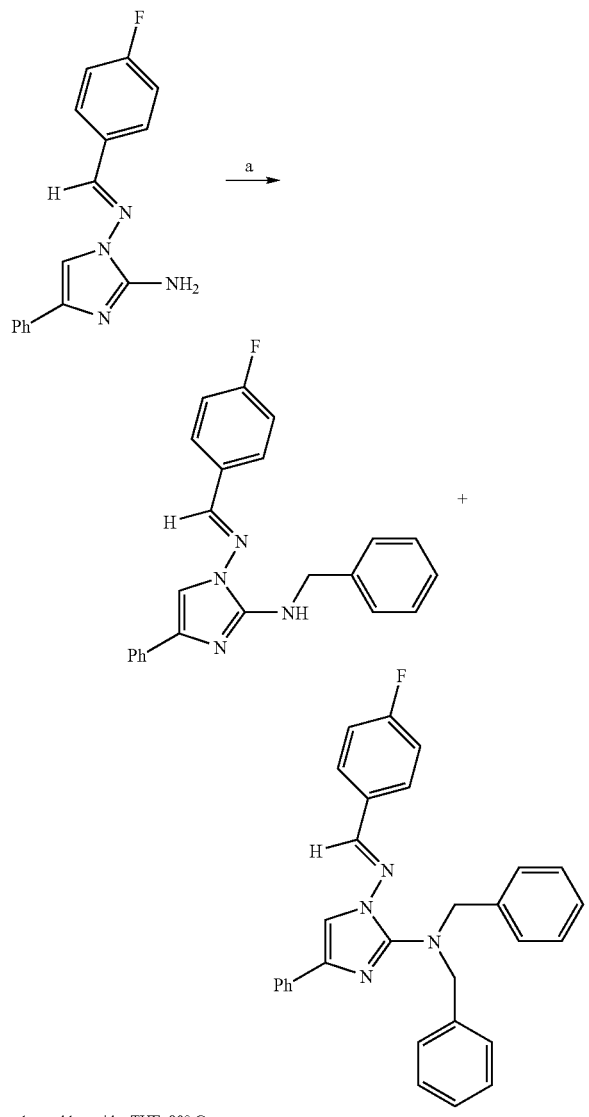

a benzyl bromide, THF, 80° C.

The imidazolamino compounds containing a thiazolyl ring at 1-N can be synthesized, as shown below in Scheme 5, by using amidinothiourea in a method similar to that depicted in Scheme 1:

Scheme 5

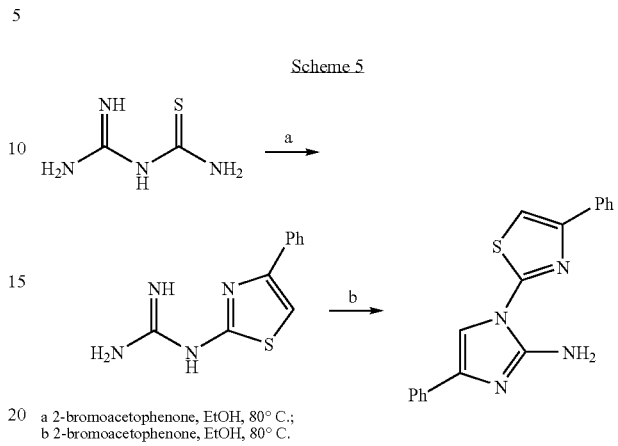

a 2-bromoacetophenone, EtOH, 80° C.;
b 2-bromoacetophenone, EtOH, 80° C.

Like other imidazolamino compounds, the 2-amino group of the above-shown thiazolylimidazolamino compound can be modified as shown in Schemes 2-4.

As mentioned above, the compounds of this invention can be used to inhibit the growth of (including killing) cancer cells. Thus, another aspect of this invention relates to a pharmaceutical composition which contains an effective amount of at least one of the compounds described above (or its salt) and a pharmaceutically acceptable carrier for treating cancer. "An effective amount" refers to the amount of the compound which is required to confer a therapeutic effect on the treated subject. The interrelationship of dosages for animals and humans (based on milligrams per meter squared of body surface) is described in Freireich et al., Cancer Chemother. Rep., 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on route of administration, excipient usage, and the possibility of co-usage with other therapeutic treatments including use of other anti-platelet aggregation agents. Examples of the carriers include colloidal silicon dioxide, magnesium stearate, cellulose, sodium lauryl sulfate, and D&C Yellow # 10.

The pharmaceutical composition may be administered via a parenteral route, e.g., topically, subcutaneously, intraperitoneally, intramuscularly, and intravenously. Examples of parenteral dosage forms include aqueous solutions of the active compound, in an isotonic saline, 5% glucose, or any other well-known pharmaceutically acceptable carrier. Solubilizing agents, such as cyclodextrins, or other solubilizing agents well known to those familiar with the art, can also be included in the pharmaceutical composition.

An imidazolamino compound of this invention can be formulated into dosage forms for other routes of administration (e.g., orally, mucosally, or percutaneously) utilizing well known methods. The pharmaceutical composition can be formulated, for example, in dosage forms for oral administration in a capsule, a gel seal, or a tablet. Capsules may comprise any well known pharmaceutically acceptable material such as gelatin or cellulose derivatives. Tablets may be formulated in accordance with the conventional procedure by compressing mixtures of the active compounds, a solid carrier, and a lubricant. Examples of solid carriers include starch and sugar bentonite. The compound can also be administered in a form of a hard shell tablet or capsule containing, for example, lactose or mannitol as a binder, a conventional filler, and a tableting agent.

As mentioned above, the imidazolamino compounds of this invention have anti-cancer activities. Their activities can be evaluated by in vitro and in vivo assays well known in the art. For instance, a panel of human cancer cell lines can be first seeded in a medium, incubated, and brought in contact with a compound. The anti-cancer (cytotoxic) acitivities can then be determined by evaluating the viability of the cells. An in vivo assay can be conducted by using mice inoculated with cancer cells, followed by administration of the compounds of this invention. The efficacy of the compound can then be confirmed by monitoring the survival rate of these mice.

Without further elaboration, it is believed that one skilled in the art can, based on the description herein, utilize the present invention to its fullest extent. All publications recited herein are hereby incorporated by reference in their entirety. The following specific examples, which describe synthesis and biological testing of various compounds of the present invention, are therefore, to be construed as merely illustrative, and not limitative of the remainder of the disclosure in any way whatsoever.

EXAMPLE 1

Synthesis of N1-[(E)-1-(4-fluorophenyl)methylidene]-4-phenyl-1H-1,2-imidazolediamine (Compound 1)

A mixture of 4-fluorobenzaldehyde (2.0 g, 15.8 mmol), 20% hydrochloric acid (4 mL) was added to an aminoguanidine bicarbonate (2.2 g, 15.8 mmol) aqueous solution. After completion of the liberation of carbon dioxide, the mixture was heated for 4 h. A solution of 40% aqueous potassium hydroxide (7 mL) was added and the mixture was heated at reflux for additional 10 min. The resulting solution was filtered, washed with water until the wash water was at pH 7, dried and recrystallized from ethanol to give 2-[(E)-1-(4-fluorophenyl)methylidene]-1-hydrazinecarboximidamide (2.6 g, 91%) as a yellow solid.

2-[(E)-1-(4-fluorophenyl)methylidene]-1-hydrazinecarboximidamide (0.74 g, 4.06 mmol) was added to a solution of 2-bromoacetophenone (0.40 g, 2.03 mmol) in ethanol (10 mL), and the reaction was heated to 70° C. for 4 h. A solution of sodium hydroxide aqueous solution was added dropwise. The yellow precipitate was formed and cooled the reaction mixture at room temperature for additional 10 h, then filtered, washed with hot water and recrystallized from ethanol to give 1 (0.44 g, 77%) as a yellow solid.

$^1$H NMR (DMSO-$d_6$): δ 8.56 (s, 1H), 8.01-7.96 (m, 3H), 7.69 (d, J=7.2 Hz, 2H), 7.37-7.30 (m, 4H), 7.18 (t, J=7.2 Hz, 1H), 6.20 (s, 2H). ESMS m/z: 281.5 (MH$^+$).

EXAMPLE 2

Synthesis of N1-[(E)-1-(4-chlorophenyl)methylidene]-4-(5-chloro-2-thienyl)-1H-1,2-imidazolediamine (Compound 2)

A mixture of 4-chlorobenzaldehyde (2.0 g, 10.2 mmol), 20% hydrochloric acid (4 mL) was added to an aminoguanidine bicarbonate (1.39 g, 10.2 mmol) aqueous solution, and heated to reflux for 4 h. A solution of 40% aqueous potassium hydroxide (7 mL) was added dropwise, the mixture was heated at reflux for 10 min and the precipitate formed. The precipitate was filtered, washed with water, and recrystallized from ethanol to give 2-[(E)-1-(4-chlorophenyl)methylidene]-1-hydrazinecarboximidamide (1.77 g, 88%) as a yellow solid.

A solution of 2-bromo-1-(5-chloro-2-thienyl)-1-ethanone (1.07 g, 4.49 mmol), 2-[(E)-1- (4-chlorophenyl)methylidene]-1-hydrazinecarboximidamide (1.77 g, 8.98 mmol) was heated in ethanol (10 mL) for 2 h, then the mixture was left at room temperature for additional 10 h. The precipitate filtered, washed with hot water, and recrystallized from ethanol to give N1-[(E)-1-(4-chlorophenyl)methylidene]-4-(5-chloro-2-thienyl)-1H-1,2-imidazolediamine 2 (1.09 g, 72%) as a brown solid.

$^1$H NMR (DMSO-$d_6$): δ 8.51 (s, 1H), 7.94 (d, J=7.8 Hz, 2H), 7.86 (s, 1H), 7.57 (d, J=7.8 Hz, 2H), 7.05 (s, 2H), 6.39 (s, 2H). ESMS m/z: 337.4 (MH$^+$).

EXAMPLE 3

Synthesis of N1-[(E)-1-(4-methoxyphenyl)methylidene]-4,5-diphenyl-1H-1,2-imidazolediamine (Compound 3)

A mixture of 4-anisaldehyde (2.0 g, 14.4 mmol), 20% hydrochloric acid (4 mL) was added to an aminoguanidine bicarbonate (1.96 g, 14.4 mmol) aqueous solution, and heated to reflux for 4 h. 40% aqueous potassium hydroxide (7 mL) was added and the mixture was heated at reflux for additional 10 min. The mixture was cooled in room temperature for 10 h and a yellow precipitate formed. The yellow precipitate was filtered, washed with hot water and recrystallized from ethanol to give 2-[(E)-1-(4-methoxyphenyl)methylidene]-1-hydrazinecarboximidamide (2.4 g, 87%) as a yellow solid.

A solution of desyl bromide (1.72 g, 6.26 mmol), and 2-[(E)-1-(4-methoxyphenyl) methylidene]-1-hydrazinecarboximidamide (2.4 g, 12.5 mmol) was heated at reflux in ethanol (10 mL) for 2 h. The mixture was cooled at room temperature for additional 10 h, and a yellow precipitate formed. The yellow precipitate was filtered, washed with hot water and recrystallized from ethanol to give N1-[(E)-1-(4-methoxyphenyl)methylidene]-4,5-diphenyl-1H-1,2-imidazolediamine 3 (1.57 g, 68%) as a yellow solid.

$^1$H NMR (DMSO-$d_6$): δ 7.91 (s, 1H), 7.52 (d, J=9.0 Hz, 2H), 7.44-7.31 (m, 6H), 7.19-7.06 (m, 4H), 6.98 (d, J=9.0 Hz, 2H), 5.92 (br, 2H), 3.79 (s, 3H). ESMS m/z: 369.1 (MH$^+$).

EXAMPLE 4

Synthesis of N1-[(E)-1-(4-fluorophenyl)methylidene]-4-(1,3-thiazol-2-yl)-1H-1,2-imidazolediamine (Compound 4)

A mixture of 4-fluorobenzaldehyde (2.0 g, 15.8 mmol), 20% hydrochloric acid (4 mL) was added to an aminoguanidine bicarbonate (2.2 g, 15.8 mmol) aqueous solution. After completion of the liberation of carbon dioxide, the mixture was heated for 4 h. A solution of 40% aqueous potassium hydroxide (7 mL) was added and the mixture was heated at reflux for additional 10 min. The resulting solution was cooled, filtered, washed with water until the wash water was at pH 7, dried and recrystallized from ethanol to give 2-[(E)-1-(4-fluorophenyl)methylidene]-1-hydrazinecarboximidamide (2.6 g, 91%) as a yellow solid.

A solution of 2-bromo-1-(1,3-thiazol-2-yl)-1-ethanone (1.5 g, 7.2 mmol), and 2-[(E)-1-(4-fluorophenyl)methylidene]-1-hydrazinecarboximidamide (2.6 g, 14.4 mmol) was heated at reflux in ethanol (10 mL) for 2 h. The mixture was left at room temperature for additional 10 h, then the precipitate was filtered, washed with hot water and recrystallized from ethanol to give N1-[(E)-1-(4-fluorophenyl)methylidene]-4-(1,3-thiazol-2-yl)-1H-1,2-imidazole diamine 4 (1.45 g, 70%) as a yellow solid.

$^1$H NMR (DMSO-$d_6$): δ 8.74 (s, 1H), 8.12 (s, 1H), 8.03-7.97 (m, 2H), 7.81-7.79 (m, 1H), 7.59-7.58 (m, 1H), 7.35 (t, J=8.0 Hz, 2H), 6.57 (br, 2H). ESMS m/z: 288.0 (MH$^+$).

EXAMPLE 5

Synthesis of 1-(4-methyl-1,3-thiazol-2-yl)-4-phenyl-1H-2-imidazolamine (Compound 5)

A mixture of amidinothiourea (2.0 g, 16.9 mmol), chloroacetone (1.56 g, 16.9 mmol) was heated at reflux in acetone (12 mL) for 4 h. The mixture was cooled to room temperature and removed half of the solvent. The precipitate was filtered, washed with dry acetone, and dried to give N-(4-methyl-1,3-thiazol-2-yl)guanidine (2.19 g, 83%).

A solution of N-(4-methyl-1,3-thiazol-2-yl)guanidine (2.19 g, 14.0 mmol) and 2-bromoacetophenone (13.9 g, 7.0 mmol) in ethanol (5 mL) was heated to 80° C. for 2 h. The mixture was left at room temperature for additional 10 h, filtered, washed with hot water and recrystallized from ethanol to give 5 (1.38 g, 77%).

$^1$H NMR (DMSO-$d_6$): δ 7.78 (d, J=7.2 Hz, 2H), 7.63 (s, 1H), 7.35 (t, J=7.2 Hz, 2H), 7.22 (t, J=7.2 Hz, 1H), 7.08 (s, 1H), 6.95 (br, 2H), 2.35 (s, 3H). ESMS m/z: 257.0 (MH$^+$), 279.0 (M+23)$^+$.

EXAMPLE 6

Synthesis of 1-(4-phenyl-1,3-thiazol-2-yl)-4-(2-thienyl)-1H-2-imidazolamine (Compound 6)

A mixture of amidinothiourea (2.0 g, 16.9 mmol), 2-bromoacetophenone (3.4 g, 16.9 mmol) was heated at reflux in acetone (12 mL) for 4 h. The mixture was cooled to room temperature and removed half of the solvent. The precipitate was filtered, washed with acetone, and dried to give N-(4-phenyl-1,3-thiazol-2-yl)guanidine (3.2 g, 87%).

A solution of N-(4-phenyl-1,3-thiazol-2-yl)guanidine (3.2 g, 14.7 mmol) and 2-bromo-1-(2-thienyl)-1-ethanone (1.5 g, 7.35 mmol) in ethanol (5 mL) was heated to 80° C. for 2 h. The mixture was left at room temperature for additional 10 h, filtered, washed with hot water and recrystallized from ethanol to give 6 (1.48 g, 62%).

$^1$H NMR (DMSO-$d_6$): δ 7.85 (d, J=6.9 Hz, 2H), 7.48-7.38 (m, 3H), 7.33 (d, J=3.3 Hz, 1H), 7.25-7.20 (m, 2H), 7.02-7.03 (m, 2H), 6.36 (br, 2H). ESMS m/z: 325.0 (MH$^+$).

EXAMPLE 7

Synthesis of 1-[4-(4-chlorophenyl)-1,3-thiazol-2-yl]-5-phenyl-1H-2-imidazolamine (Compound 7)

A mixture of amidinothiourea (2.0 g, 16.9 mmol), 2-bromoacetophenone (3.4 g, 16.9 mmol) was heated at reflux in acetone (12 mL) for 4 h. The mixture was cooled to room temperature and removed half of the solvent. The precipitate was filtered, washed with acetone, and dried to give N-(4-phenyl-1,3-thiazol-2-yl)guanidine (3.2 g, 87%).

A solution of N-(4-phenyl-1,3-thiazol-2-yl)guanidine (3.2 g, 14.7 mmol) and 2-bromo-2-phenylacetaldehyde (1.46 g, 7.3 mmol) in ethanol (5 mL) was heated to 80° C. for 2 h. The mixture was left at room temperature for additional 10 h, filtered, washed with hot water and recrystallized from ethanol to give 7 (1.65 g, 71%).

$^1$H NMR (CDCl$_3$): δ 8.08 (s, 1H), 7.99 (d, J=8.4 Hz, 2H), 7.52 (d, J=8.4 Hz, 2H), 7.35-7.19 (m, 5H), 6.82 (s, 1H), 6.50 (br, 2H). ESMS m/z: 353.0 (MH$^+$).

EXAMPLE 8

Synthesis of 2,4-dibromo-6-[(1-[(E)-1-(4-fluorophenyl)methylidene]amino-4-phenyl-1H-2-imidazolyl)imino]methylphenol (Compound 8)

A mixture of 4-fluorobenzaldehyde (2.0 g, 15.8 mmol), 20% hydrochloric acid (4 mL) was added to an aminoguanidine bicarbonate (2.2 g, 15.8 mmol) aqueous solution. After completion of the liberation of carbon dioxide, the mixture was heated for 4 h. A solution of 40% aqueous potassium hydroxide (7 mL) was added and the mixture was heated at reflux for additional 10 min. The resulting solution was filtered, washed with water until the wash water was at pH=7, dried and recrystallized from ethanol to give 2-[(E)-1-(4-fluorophenyl)methylidene]-1-hydrazinecarboximidamide (2.6 g, 91%) as a yellow solid.

A solution of sodium hydroxide (81 mg, 2.03 mmol) in ethanol (5 mL) was added dropwise over 20 min to a mixture of 2-bromoacetophenone (0.40 g, 2.03 mmol), and 2-[(E)-1-(4-fluorophenyl)methylidene]-1-hydrazinecarboximidamide (0.37 g, 2.03 mmol) in ethanol (10 mL). The reaction was heated to 70° C. for 2 h, and a yellow precipitate formed. The mixture was cooled at room temperature for additional 10 h, then filtered, washed with hot water and recrystallized from ethanol to give 1 (0.44 g, 77%) as a yellow solid.

To a solution of N1-[(E)-1-(4-fluorophenyl)methylidene]-4-phenyl-1H-1,2-imidazole diamine 1 (0.44 g, 1.56 mmol) and 3,5-dibromosalicylaldehyde (0.44 g, 1.56 mmol) was dissolved in EtOH (20 mL). The mixture was heated to reflux for 2 h, and stirred at room temperature for further 2 h. The resulting solution was filtered, washed with hot water, and recrystallized from ethanol to give 8 (0.7 g, 83%) as a yellow solid.

$^1$H NMR (DMSO-$d_6$): δ 9.41 (s, 1H), 9.01 (s, 1H), 8.67 (s, 1H), 8.12 (d, J=2.1 Hz, 1H), 7.98-7.92 (m, 3H), 7.88 (d, J=8.7 Hz, 2H), 7.49-7.43 (m, 4H), 7.32 (t, J=7.5 Hz, 1H). ESMS m/z: 540.1 (MH$^+$).

EXAMPLES 9-33

The following compounds were synthesized according to the methods described above:

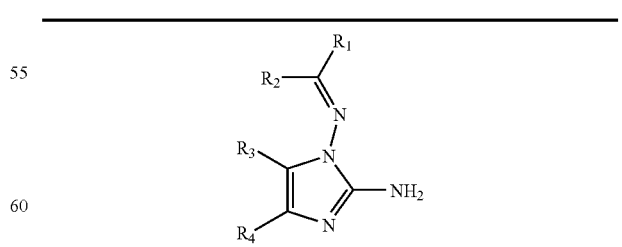

| Compound | R$^1$ | R$^2$ | R$^3$ | R$^4$ |
|---|---|---|---|---|
| 9 | 3-methyl-2-thienyl | H | H | phenyl |
| 10 | 4-(trifluoromethyl)phenyl | H | H | phenyl |

-continued

| Compound | R¹ | R² | R³ | R⁴ |
|---|---|---|---|---|
| 11 | 4-chloro-2-nitrophenyl | H | H | phenyl |
| 12 | 3,4-dichlorophenyl | H | H | phenyl |
| 13 | 2,3-dichlorophenyl | H | H | Phenyl |
| 14 | 2-chlorophenyl | H | H | Phenyl |
| 15 | 4-quinolyl | H | H | Phenyl |
| 16 | 10-chloro-9-anthryl | H | H | phenyl |
| 17 | 4-chlorophenyl | H | H | biphenyl |
| 18 | 4-chlorophenyl | H | H | 2-methoxyphenyl |
| 19 | 4-fluorophenyl | H | H | 3-thienyl |
| 20 | 4-chlorophenyl | H | H | 3-thienyl |
| 21 | 4-chlorophenyl | H | H | 2,4-dimethylphenyl |
| 22 | 4-fluorophenyl | H | H | 2-pyridyl |
| 23 | 4-chlorophenyl | H | H | 2-pyridyl |
| 24 | 4-fluorophenyl | H | H | 3-pyridyl |
| 25 | 4-chlorophenyl | H | H | 3-pyridyl |
| 26 | 4-fluorophenyl | H | H | 2-thienyl |
| 27 | 4-chlorophenyl | H | H | 2-thienyl |
| 28 | 4-fluorophenyl | H | H | 2,4-dichlorophenyl |
| 29 | 4-chlorophenyl | H | H | 2,4-dichlorophenyl |
| 30 | 4-chlorophenyl | H | H | 2-naphthyl |
| 31 | 4-fluorophenyl | H | phenyl | phenyl |
| 32 | 4-chlorophenyl | H | phenyl | Phenyl |
| 33 | 4-chlorophenyl | H | H | 1,3-thiazol-2-yl |

EXAMPLES 34-59

The following compounds were synthesized according to the methods described above:

| Compound | R¹ | R² | R³ |
|---|---|---|---|
| 34 | phenyl | H | phenyl |
| 35 | 3-thienyl | H | phenyl |
| 36 | 2-pyridyl | H | phenyl |
| 37 | 4-chlorophenyl | H | Phenyl |
| 38 | 5-chloro-2-thienyl | H | phenyl |
| 39 | 2-thienyl | H | phenyl |
| 40 | 1,3-thiazol-2-yl | H | phenyl |
| 41 | phenyl | H | 4-fluorophenyl |
| 42 | phenyl | H | 2-naphthyl |
| 43 | 2-chlorophenyl | H | 2-thienyl |
| 44 | 2-pyridyl | H | 2-thienyl |
| 45 | methyl | H | 2-thienyl |
| 46 | 2-pyridyl | H | 2-pyridyl |
| 47 | phenyl | H | 2-pyridyl |
| 48 | methyl | H | 2-pyridyl |
| 49 | 5-chloro-2-thienyl | H | 3-thienyl |
| 50 | phenyl | H | 3-thienyl |
| 51 | 3-thienyl | H | 3-thienyl |
| 52 | phenyl | H | 5-chloro-2-thienyl |
| 53 | 3-thienyl | H | 3-thienyl |
| 54 | phenyl | H | 2-furyl |
| 55 | phenyl | phenyl | H |
| 56 | phenyl | phenyl | phenyl |
| 57 | 4-chlorophenyl | H | 1,3-thiazol-2-yl |
| 58 | methyl | H | 1,3-thiazol-2-yl |
| 59 | phenyl | H | 1,3-thiazol-2-yl |

EXAMPLES 60-65

The following compounds were synthesized according to the methods described above:

| Compound | R¹ | R² | R³ | R⁴ | R⁵ | R⁶ |
|---|---|---|---|---|---|---|
| 60 | 4-fluorophenyl | H | H | phenyl | 2-hydroxyphenyl | H |
| 61 | 4-chlorophenyl | H | H | phenyl | 5-bromo-2-hydroxy-3-methoxyphenyl | H |
| 62 | 4-chlorophenyl | H | H | phenyl | 2-hydroxyphenyl | H |
| 63 | 4-fluorophenyl | H | H | Phenyl | 3,5-dichloro-2-hydroxyphenyl | H |
| 64 | 4-fluorophenyl | H | H | Phenyl | 5-bromo-2-hydroxy-3-methoxyphenyl | H |
| 65 | 4-chlorophenyl | H | H | 1,3-thiazol-2-yl | 3,5-dibromo-2-hydroxyphenyl | H |

EXAMPLES 66-75

The following compounds were synthesized according to the methods described above:

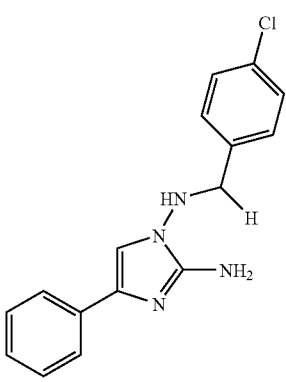

| Compound | R¹ | R² | R³ | R⁴ | R⁵ |
|---|---|---|---|---|---|
| 66 | 4-chlorophenyl | H | H | phenyl | 4-chlorobenzyl |
| 67 | 4-fluorophenyl | H | H | phenyl | [5-(dimethylamino)-1-naphthyl]sulfonyl |
| 68 | 4-chlorophenyl | H | H | phenyl | 4-[5-(dimethylamino)-1-naphthyl]sulfonyl |
| 69 | 4-chlorophenyl | H | H | phenyl | 1,3-benzodioxole-5-carbonyl |
| 70 | 4-chlorophenyl | H | H | phenyl | 2-naphthalenecarbonyl |
| 71 | 4-chlorophenyl | H | H | phenyl | 4-bromo-1-benzenecarbonyl |
| 72 | 4-fluorophenyl | H | H | phenyl | 4-cyano-1-benzenecarbonyl |
| 73 | 4-fluorophenyl | H | H | phenyl | (1-methyl-1H-2-imidazolyl)methyl |
| 74 | 4-chlorophenyl | H | H | phenyl | 4-bromo-1-benzenesulfonyl |
| 75 | 4-fluorophenyl | H | H | phenyl | 4-bromo-1-benzenesulfonyl |

EXAMPLES 76-99

The following compounds were synthesized according to the methods described above:

76

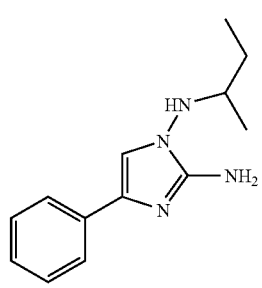

77

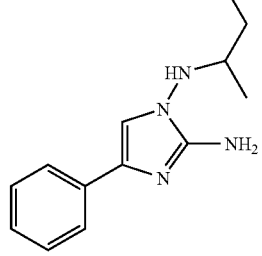

78

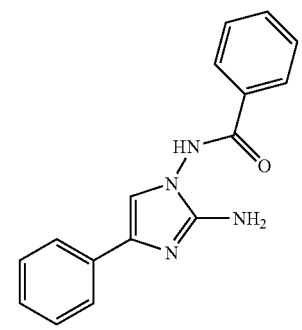

79

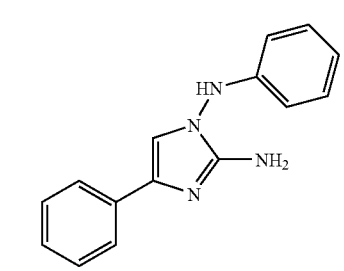

80

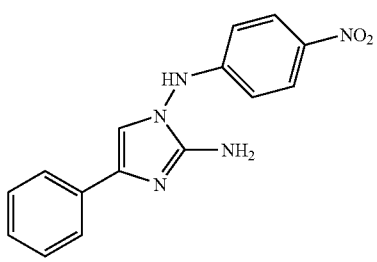

81

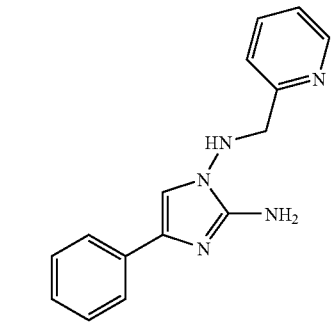

82

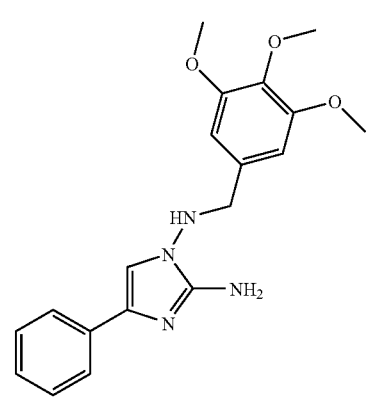

83
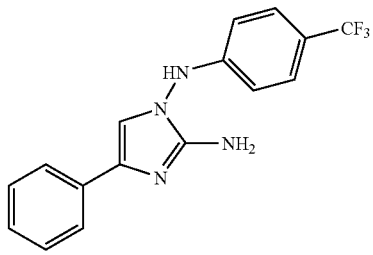
84
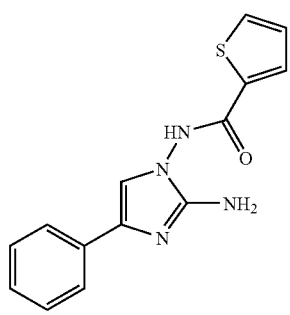
85
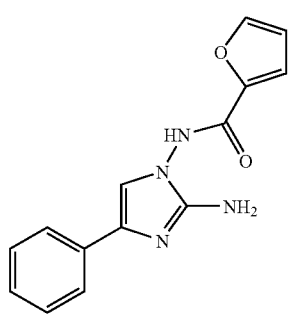
86
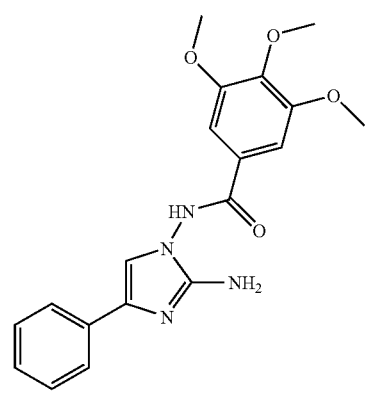
87
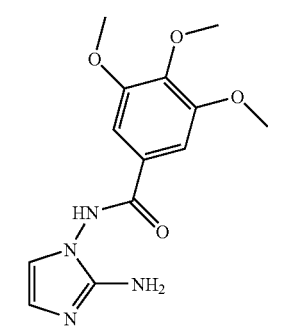
88
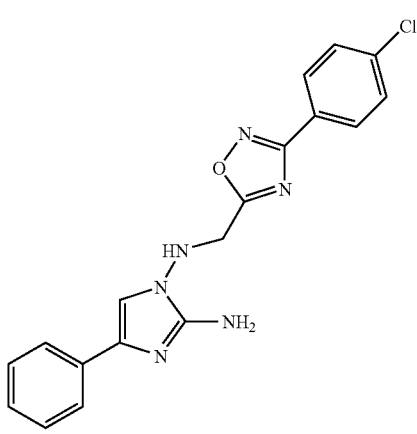
89
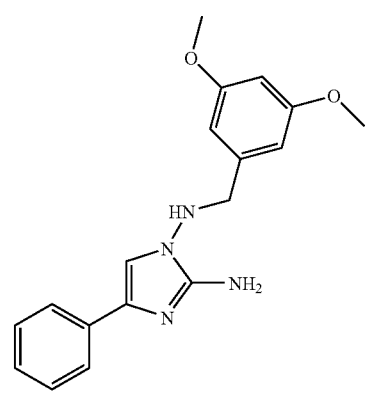
90
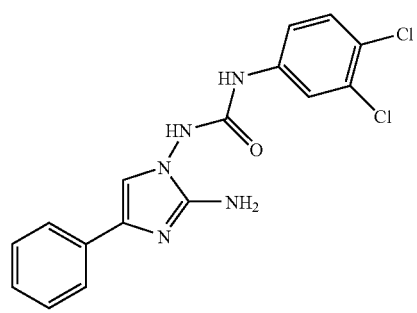
91
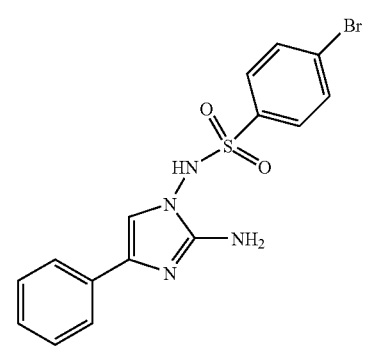

-continued

92 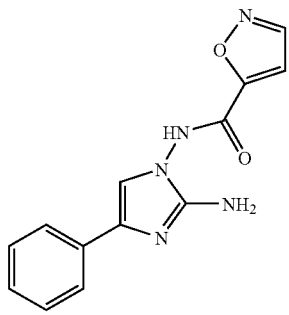

93 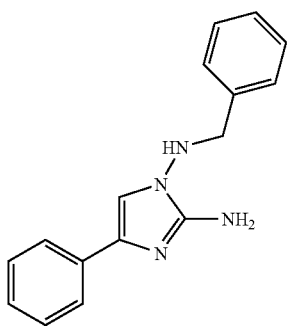

94 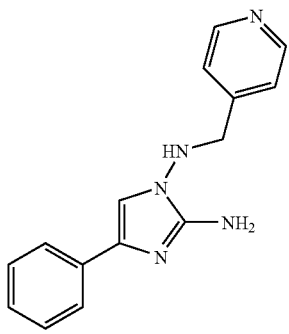

95 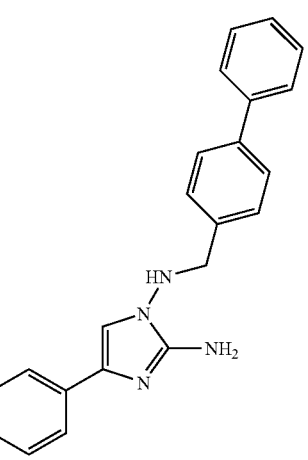

96 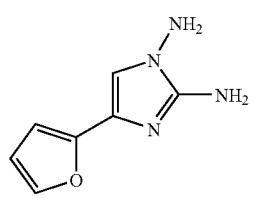

-continued

97 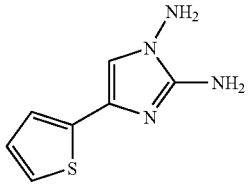

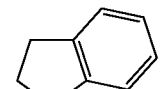

98 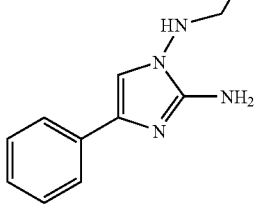

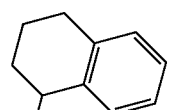

99 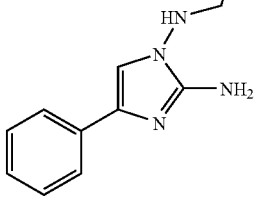

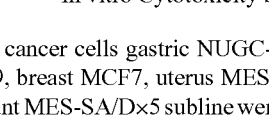

EXAMPLE 100

In vitro Cytotoxicity Study

Human cancer cells gastric NUGC-3, colorectal SW480, lung A549, breast MCF7, uterus MES-SA, and its adriamycin-resistant MES-SA/Dx5 subline were used in in vitro cytotoxicity assays. The human cells were seeded at a cell density of 3000 or 4500 cells/100 µl/well in 96-well flat-bottom plates and incubated for 24 hours at 37° C. in a 5% $CO_2$ incubator. The compounds to be tested were dissolved in dimethyl sulfoxide (DMSO) and further diluted into the culture medium for inhibiting (killing) these human cancer cells in vitro to have a final DMSO concentration of 0.3%. Nine compounds of this invention, i.e., Compounds 6, 73, 74, 72, 71, 69, 68, 70, and 75, were prepared in culture media for testing at a range of concentrations from 10, 1, 0.1, 0.01 to 0.001 µM. Each compound solution (200 µl/well) was duplicated in two wells of the cell plates and was treated for 72 hours at 37° C., 5% $CO_2$ in an incubator. 0.3% DMSO was used as the vehicle control. A colorimetric assay using 3-(4,5-dimethylthiazol-2-yl)-5-(3-carboxymethoxyphenyl)-2-(4-sulfophenyl)-2H-tetrazolium (MTS) and phenazine methosulfate (PMS) was used to determine the potency of the tested compounds. This assay measured cell viability based on the cellular activity in conversion of a tetrazolium salt into a colored soluble formazan product. The optical density (OD)

values were measured at 490 nm with a 1420 multilabel counter VICTOR® from Wallac (Turku, Finland). All of the measured values were subtracted with that of the blank control wells without cells before further calculations. The efficacy data are expressed as a percentage normalized to the vehicle controls as calculated in the following formulae. Inhibitory potency (% of vehicle control)=[($OD490_{compound}$−$OD490_{blank}$)/($OD490_{vehicle}$−$OD490_{blank}$)]×100%. The concentration of a test compound that inhibits 50% of the cellular activity ($IC_{50}$) was determined.

All the tested compounds unexpectedly exhibited a broad spectrum of anticancer activities among all the six used human cancer cell lines.

EXAMPLE 101

Evaluation of In vivo Anticancer Activity

The in vivo anticancer activities of the compounds were evaluated by the following murine leukemic P388 model. Inbred female DBA/2J mice of 4-5 week-old were purchased from the National Laboratory Animals Breeding and Research Center, Taipei, Taiwan, ROC. Murine leukemic P388 cells were purchased from the Japanese Collection of Research Bioresources, Japan. P388 cells were cultured and propagated in RPMI1640 medium supplemented with 50 μM 2-mercaptoethanol and 10% fetal bovine serum. Mice at the age of 6 weeks were grouped as the treatment, negative control and positive control groups at 7 to 8 mice per group. All mice were intravenously inoculated with the P388 cells at one million per mouse one day before the treatments initiated. Compound 6 was dissolved in dimethyl sulfoxide (DMSO) and then diluted in 0.5% carboxymethyl cellulose or a Cremophor-based vehicle with the final concentration of DMSO less than 0.5%. Different treatment groups were orally (P.O.) or intravenously (I.V.) given, respectively, with Compound 6 of different doses for a pharmacological dose-response relationship. The mice of the negative control group were treated with the dosing vehicle only. A positive control, doxorubicin 10 mg/kg given by an intravenous injection, was included. The cancer cell-inoculated animals were monitored twice daily. Survival fractions of the mice were recorded. The time on which 50% of the P388-inoculated mice were still surviving is defined as the medium survival time and was used to calculate the percentage (normalized to the medium survival time of the control group) of increased in life span after treatment, which was then served as the index of treatment response.

The results showed that Compound 6 unexpectedly increased the survival rate of the inoculated mice.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:
1. A compound of the following formula:

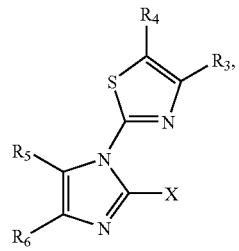

wherein
X is —$NR_aR_b$ or —N=$CR_cR_d$, in which each of $R_a$ and $R_b$, independently, is hydrogen, halo, alkyl, or haloalkyl; arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl, and each of $R_c$ and $R_d$, independently, is hydrogen; halo; alkyl; heteroaryl; phenyl optionally substituted with hydroxy, halo, alkyl, haloalkyl, alkoxy, or amino; phenylsulfonyl substituted with cyano, halo, or amino; phenylcarbonyl substituted with cyano, halo, or amino; naphthylsulfonyl substituted with cyano, halo, or amino; naphthylcarbonyl substituted with cyano, halo, or amino; or alkyl optionally substituted with halo, phenyl or imidazolyl, or phenyl or imidazolyl optionally substituted with alkyl, halo, or hydroxy;
$R_3$ is alkyl, phenyl, thienyl, pyridinyl, thiazolyl, cycloalkyl, cycloalkenyl, benzofuranyl, indolyl, pyrazinyl, pyrimidinyl, pyrrolyl, N-methylpyrrolyl, isothiazolyl, oxadiazolyl, furyl, isoazolyl, oxazolyl, or heterocyclyl optionally substituted with halo, alkyl, haloalkyl, hydroxy, or amino;
$R_4$ is hydrogen, alkyl, hydroxy, or amino;
$R_5$ is hydrogen, alkyl, or aryl optionally substituted with hydroxy, halo, alkyl, haloalkyl, or amino;
$R_6$ is hydrogen, fluorophenyl, naphthyl, thienyl, pyridinyl, furyl, thiazolyl cycloalkyl, cycloalkenyl, benzofuranyl, indolyl, pyrazinyl, pyrimidinyl, pyrrolyl, N-methylpyrrolyl, isothiazolyl, oxadiazolyl, isoazolyl, oxazolyl, or heterocyclyl when $R_3$ is alkyl optionally substituted with halo, hydroxy, or amino, or is phenyl optionally substituted with halo, hydroxy, amino, or alkyl; and $R_5$ is hydrogen, alkyl, or aryl optionally substituted with hydroxy, alkyl, or amino, or is phenyl optionally substituted with hydroxy, halo, alkyl, haloalkyl, or amino when $R_3$ is thienyl, pyridinyl, or thiazolyl, optionally substituted with halo, alkyl, haloalkyl, or hydroxy, and $R_3$ is hydrogen, alkyl, or phenyl optionally substituted with hydroxy, halo, alkyl, haloalkyl, or amino.

2. The compound of claim 1, wherein $R_3$ is alkyl optionally substituted with halo, hydroxy, or amino, or is phenyl optionally substituted with halo, hydroxy, amino, or alkyl; $R_5$ is hydrogen, alkyl, or aryl optionally substituted with hydroxy, alkyl, or amino; and $R_6$ is hydrogen, fluorophenyl, naphthyl, thienyl, pyridinyl, furyl, or thizaolyl.

3. The compound of claim 2, wherein $R_6$ is hydrogen, naphthyl, thienyl, furyl, or thiazolyl.

4. The compound of claim 3, wherein X is $NH_2$; and $R_4$ is H.

5. The compound of claim 4, wherein $R_3$ is phenyl or alkyl, optionally substituted with halo; and $R_5$ is hydrogen or phenyl.

6. The compound of claim 1, wherein $R_3$ is thienyl, pyridinyl, or thiazolyl, optionally substituted with hydroxy, halo, alkyl, or haloalkyl; $R_5$ is hydrogen, alkyl, or phenyl optionally substituted with hydroxy, halo, alkyl, haloalkyl, or amino; and $R_6$ is phenyl optionally substituted with hydroxy, halo, alkyl, haloalkyl, or amino.

7. The compound of claim 6, wherein $R_6$ is phenyl.

8. The compound of claim 7, wherein X is $NH_2$; and $R_4$ is H.

9. The compound of claim 8, wherein $R_3$ is thienyl, pyridinyl, or thiazolyl, optionally substituted with halo; and $R_5$ is hydrogen or phenyl.

10. The compound of claim 1, wherein the compound is

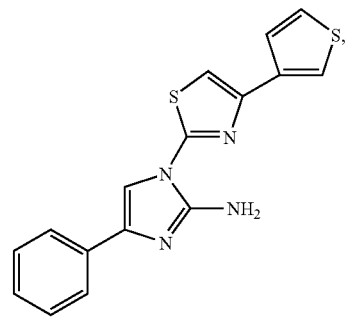

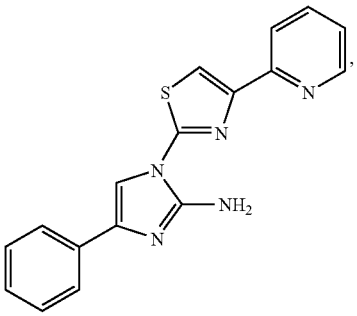

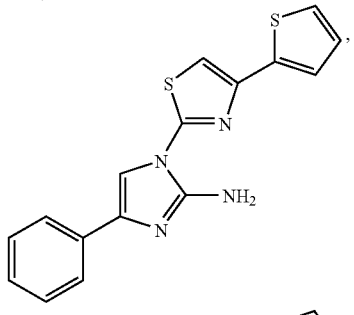

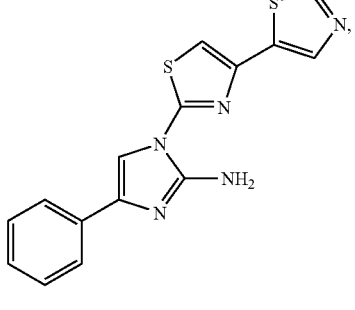

-continued

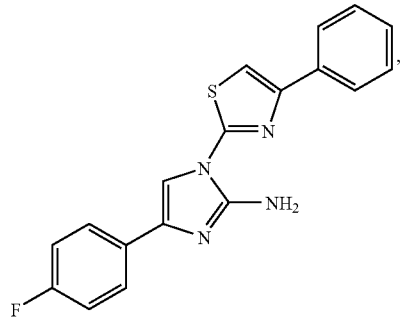

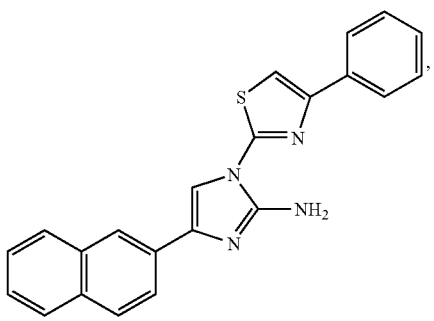

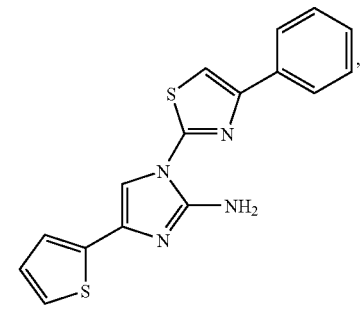

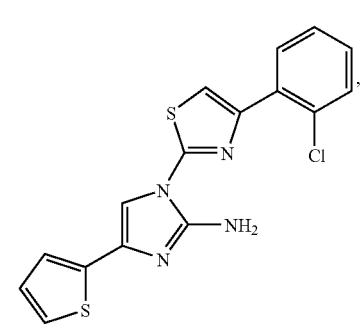

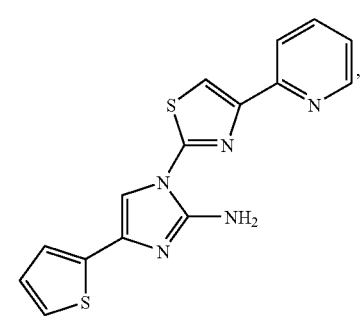

-continued
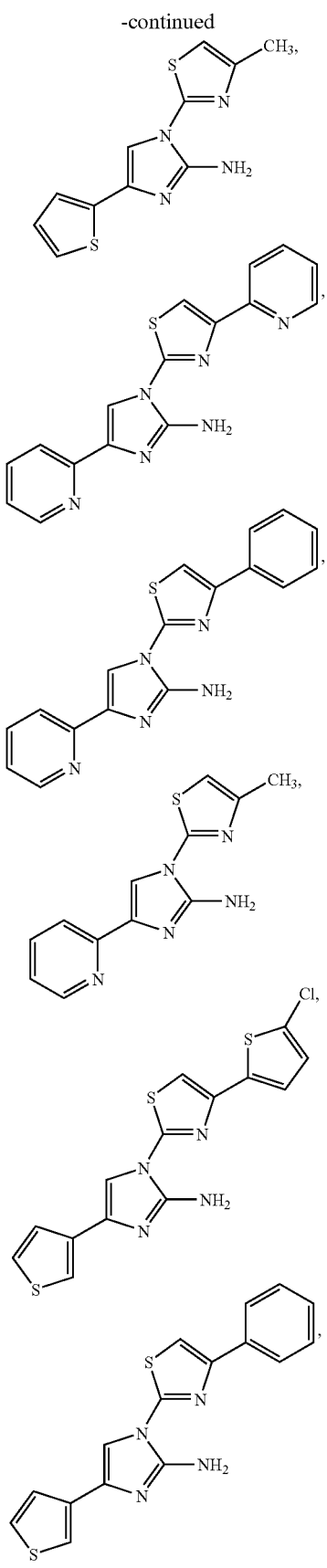
-continued
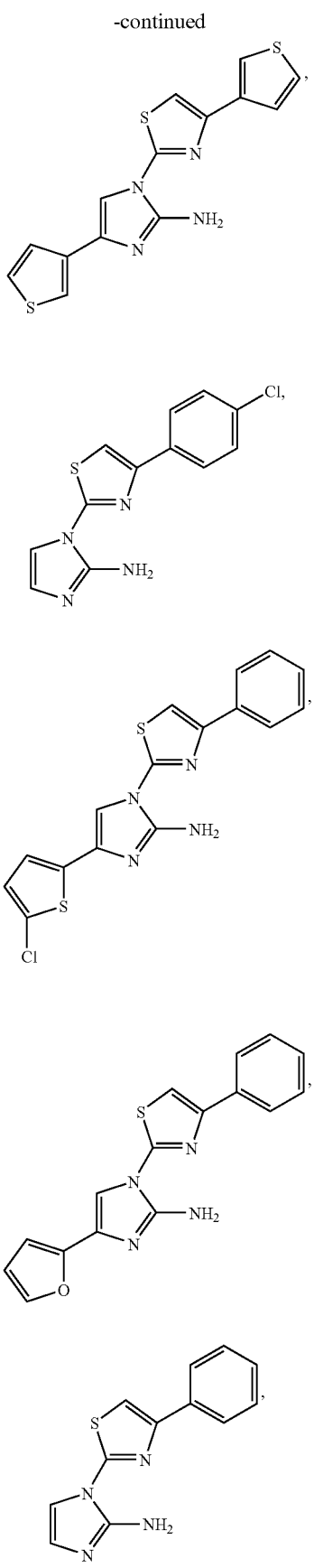

-continued

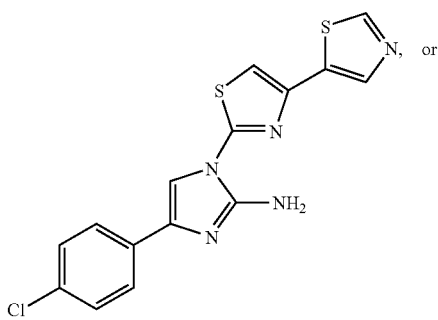

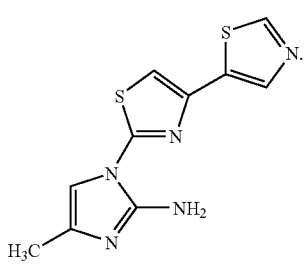

11. A pharmaceutical composition comprising a pharmaceutically acceptable carrier and a compound of the following formula:

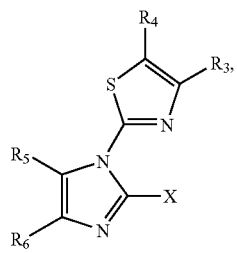

wherein

X is —$NR_aR_b$ or —$N=CR_cR_d$, in which each of $R_a$ and $R_b$, independently, is hydrogen, halo, alkyl, or haloalkyl; arylalkyl, heteroarylalkyl, arylcarbonyl, heteroarylcarbonyl, arylaminocarbonyl, or arylsulfonyl, in which aryl or heteroaryl is optionally substituted with alkoxy, halo, nitro, cyano, haloalkyl, and each of $R_c$ and $R_d$, independently, is hydrogen; halo; alkyl; heteroaryl; phenyl optionally substituted with hydroxy, halo, alkyl, haloalkyl, alkoxy, or amino; phenylsulfonyl substituted with cyano, halo, or amino; phenylcarbonyl substituted with cyano, halo, or amino; naphthylsulfonyl substituted with cyano, halo, oxo, or amino; naphthylcarbonyl substituted with cyano, halo, or amino; or alkyl optionally substituted with halo, phenyl or imidazolyl, or phenyl or imidazolyl optionally substituted with alkyl, halo, or hydroxy;

$R_3$ is alkyl, phenyl, thienyl, pyridinyl, thiazolyl, cycloalkyl, cycloalkenyl, benzofuranyl, indolyl, pyrazinyl, pyrimidinyl, pyrrolyl, N-methylpyrrolyl, isothiazolyl, oxadiazolyl, furyl, isoazolyl, oxazolyl, or heterocyclyl optionally substituted with halo, alkyl, haloalkyl, hydroxy, or amino;

$R_4$ is hydrogen, alkyl, hydroxy, or amino;

$R_5$ is hydrogen, alkyl, or aryl optionally substituted with hydroxy, halo, alkyl, haloalkyl, or amino;

$R_6$ is hydrogen, fluorophenyl, naphthyl, thienyl, pyridinyl, furyl, thiazolyl cycloalkyl, cycloalkenyl, benzofuranyl, indolyl, pyrazinyl, pyrimidinyl, pyrrolyl, N-methylpyrrolyl, isothiazolyl, oxadiazolyl, isoazolyl, oxazolyl, or heterocyclyl when $R_3$ is alkyl optionally substituted with halo, hydroxy, or amino, or is phenyl optionally substituted with halo, hydroxy, amino, or alkyl; and $R_5$ is hydrogen, alkyl, or aryl optionally substituted with hydroxy, alkyl, or amino, or is phenyl optionally substituted with hydroxy, halo, alkyl, haloalkyl, or amino when $R_3$ is thienyl, pyridinyl, or thiazolyl, optionally substituted with halo, alkyl, haloalkyl, or hydroxy, and $R_3$ is hydrogen, alkyl, or phenyl optionally substituted with hydroxy, halo, alkyl, haloalkyl, or amino.

* * * * *